(12) United States Patent
Bolton et al.

(10) Patent No.: US 9,713,789 B2
(45) Date of Patent: Jul. 25, 2017

(54) TREATMENT OF ALCOHOL COMPOSITIONS (71) Applicants: BP P.L.C., London (GB); Leslie William Bolton, Middlesex (GB); John Glenn Sunley, East Yorkshire (GB)

(72) Inventors: Leslie William Bolton, Middlesex (GB); John Glenn Sunley, East Yorkshire (GB)

(73) Assignee: BP P.L.C., London (GB)

( * ) Notice: Subject to any disclaimer, the term of this patent is extended or adjusted under 35 U.S.C. 154(b) by 0 days.

(21) Appl. No.: 15/027,401

(22) PCT Filed: Oct. 3, 2014

(86) PCT No.: PCT/EP2014/071265
§ 371 (c)(1),
(2) Date: Apr. 5, 2016

(87) PCT Pub. No.: WO2015/052096
PCT Pub. Date: Apr. 16, 2015

(65) Prior Publication Data
US 2016/0250586 A1    Sep. 1, 2016

(30) Foreign Application Priority Data
Oct. 8, 2013 (EP) ..................... 13187720

(51) Int. Cl.
| *B01D 53/28* | (2006.01) |
| *B01D 53/26* | (2006.01) |
| *B01D 15/00* | (2006.01) |
| *C07C 29/76* | (2006.01) |
| *C10L 1/02* | (2006.01) |
| *C12P 7/06* | (2006.01) |
| *C12P 7/16* | (2006.01) |

(52) U.S. Cl.
CPC .......... *B01D 53/261* (2013.01); *B01D 15/00* (2013.01); *B01D 53/28* (2013.01); *C07C 29/76* (2013.01); *C10L 1/02* (2013.01); *B01D 2253/108* (2013.01); *B01D 2253/116* (2013.01); *C10L 2200/0469* (2013.01); *C10L 2290/542* (2013.01); *C12P 7/06* (2013.01); *C12P 7/16* (2013.01)

(58) Field of Classification Search
CPC ...... B01D 53/261; B01D 53/28; B01D 15/00; B01D 2253/116; C10L 1/02; C10L 2290/542; C10L 2200/0469; C07C 29/76
See application file for complete search history.

(56) References Cited

U.S. PATENT DOCUMENTS

| 4,407,662 A * | 10/1983 | Ginder ................. B01D 53/261 203/19 |
| 2010/0081851 A1* | 4/2010 | Cohen .................... B01D 53/02 568/917 |
| 2011/0190550 A1* | 8/2011 | Horton .................. C07C 29/149 568/885 |

FOREIGN PATENT DOCUMENTS

| EP | 0 092 208 A2 | 10/1983 |
| FR | 2 850 963 A1 | 8/2004 |
| WO | WO 2011/097214 A2 | 8/2011 |

* cited by examiner

*Primary Examiner* — Sudhakar Katakam
(74) *Attorney, Agent, or Firm* — Nixon & Vanderhye P.C.

(57) ABSTRACT

Process for reducing the water and carboxylic acid content of an alcohol composition containing at least one alcohol having one to four carbon atoms, water and at least one carboxylic acid having from one to four carbon atoms by contacting the alcohol composition with a desiccant bed containing at least one porous inorganic oxide material at elevated temperature. At least one of the porous inorganic oxide material(s) contains Brønsted acid sites and/or neutralized Brønsted acid sites.

20 Claims, 6 Drawing Sheets

TREATMENT OF ALCOHOL COMPOSITIONS

This application is the U.S. national phase of International Application No. PCT/EP2014/071265 filed Oct. 3, 2014 which designated the U.S. and claims priority to European Patent Application No. 13187720.1 filed Oct. 8, 2013, the entire contents of each of which are hereby incorporated by reference.

This invention provides a process for the reduction of water and carboxylic acid content of an alcohols composition. Also provided is a process for the preparation of a fuel ethanol composition from an ethanol composition comprising water and acetic acid.

BACKGROUND OF THE INVENTION

Alcohols and other oxygenate compounds are being increasingly used in gasoline compositions for many reasons. Ethanol in particular is being increasingly used in gasoline, and in many jurisdictions the regular grade gasoline available through retail channels contains ethanol.

Alcohols may be obtained through a variety of routes including: synthetic preparation, for example alcohols may be derived from synthesis gas, hydrogenation of carboxylic acids or esters, or by the hydration of alkenes; extraction from natural sources, such as natural fats and oils; and preparation by the fermentation of biomass.

In recent years, there has been considerable interest in the preparation of alcohols by fermentation processes; in particular, since ethanol may be used as a biofuel component in gasoline, there has been particular interest in the preparation of ethanol by the fermentation of biomass. The term "biomass" as used herein refers to any source of organic material from biological origin. Examples of fermentation processes include the direct fermentation of biomass, such as sources of a carbohydrate, to alcohol(s) as well as the fermentation of derivatives of biomass to alcohols. For instance, bioethanol may be obtained by fermentation of feedstocks derived from sugar cane, such as sugar cane molasses and sugar cane juice; sugar beet, such as sugar beet molasses and sugar beet juice; cereal crops, such as corn or wheat, and cereal crop derived feedstocks, such as corn syrup; and lignocellulosic materials, such as fast growing grasses or "energy grasses".

Alcohols may also be derived from a fermentation process performed on a feed stream comprising carbon monoxide and hydrogen, such as synthesis gas; such processes are referenced and described in WO 2012/062633 A1.

Alcohols may also be prepared via the hydrogenation of carboxylic acids and/or esters. For example WO 2009/063176 A1 discloses a process for the conversion of ethanoic acid into ethanol characterised by the following steps:
1. introducing ethanoic acid and $H_2$ into a primary hydrogenation unit in the presence of a precious metal-based catalyst to produce ethanol and ethyl ethanoate,
2. introducing ethyl ethanoate, from step 1, together with $H_2$, into a secondary hydrogenation unit in the presence of a copper-based catalyst to produce ethanol, and
3. recovering ethanol from step 2.

WO 2010/067079 A1 discloses a process for the preparation of alcohol(s) from alkyl ester(s) wherein hydrogen, carbon monoxide and at least one alkyl ester are brought into contact with a hydrogenation catalyst comprising copper and manganese in a reaction zone to produce at least one alcohol, wherein the molar ratio of hydrogen to carbon monoxide in the reaction zone is in the range of from 100:1 to 1:10.

WO 2009/063173 A1 discloses a process for the production of ethanol from ethanoic acid and $H_2$, characterised by the following steps:
1) introducing ethanoic acid, together with methanol and/or ethanol into an esterification reactor to produce methyl ethanoate and/or ethyl ethanoate,
2) introducing ethanoate from step 1, together with $H_2$, into a hydrogenation unit to produce a stream comprising ethanol, unreacted ethanoate and optionally methanol,
3) separating the resulting stream, from step 2, into unreacted ethanoate and ethanol and optionally methanol,
4) optionally reintroducing ethanoate, from step 3, into the esterification reactor of step 1,
5) using at least a part of the methanol and/or the ethanol of step 3, as the methanol and/or ethanol feed of the esterification reactor of step 1, and
6) recovering ethanol, from step 3.

Due to the requirements in the properties of gasoline, and in order to meet various gasoline specifications around the world, any alcohols or other oxygenate compounds that are to be used in gasoline compositions must be compatible with the base gasoline that it is blended with and must not introduce contaminants that would cause the thus formed gasoline to fail to meet the required properties or specifications. As such, it is necessary to control the levels of certain contaminants in alcohols and other oxygenates that are to be used in gasoline.

Due to the nature of alcohols, in particular the lower alcohols (having from one to four carbon atoms) and especially ethanol, water is often present in significant amounts as it tends to be miscible with lower alcohols and can frequently be difficult to remove, for example due to azeotropic behaviour of water and ethanol mixtures. Additionally, certain methods for the preparation of alcohols either use organic acids during the synthesis process or may lead to the production of trace amounts of organic acids as by-products. The presence of water and acids in gasoline is very strictly limited, and, consequently, the amount of water and acid in alcohol compositions that are to be blended in to gasoline would also be required to be limited.

The use of various desiccants for the drying of solvents, including alcohol compositions, is known in the art, including the use of certain molecular sieves. The use of molecular sieve 3A for the drying of ethanol is known in the art.

The removal of acetic acid from fuel ethanol using ion-exchange resins has been reported in 'Removal of Acetic Acid from Fuel Ethanol Using Ion-Exchange Resin' by Huisheng Lv, Yanpeng Sun, Mihua Zhang, Zhonfeng Geng and Miaomiao Ren in Energy Fuels, 26, 7299 (2012). In this article, ethanol compositions containing acetic acid were treated using basic ion-exchange resins in order to reduce the acidity of the composition.

SUMMARY OF THE INVENTION

There exists a need in the art for a process which can reduce both the amount of water and the acidity in alcohol compositions for use in fuels.

BRIEF DESCRIPTION OF THE DRAWINGS

The invention is further described with reference to the accompanying drawings, in which.

DETAILED DESCRIPTION OF THE INVENTION

The present invention provides a process for reducing the water and carboxylic acid content of an alcohol composition comprising at least one alcohol having one to four carbon atoms, water and at least one carboxylic acid having from one to four carbon atoms, wherein said process comprises contacting the alcohol composition with a desiccant bed comprising at least one porous inorganic oxide material at elevated temperature, wherein at least one of the porous inorganic oxide material(s) contains Brønsted acid sites and/or neutralised Brønsted acid sites.

The present invention also provides a process for reducing the acetic acid content of an ethanol composition comprising ethanol, water and acetic acid, wherein said process comprises contacting the ethanol composition with a desiccant bed comprising at least one porous inorganic oxide material at elevated temperature, wherein at least one of the porous inorganic oxide material(s) contains Brønsted acid sites and/or neutralised Brønsted acid sites.

The present invention also provides a process for the preparation of a fuel ethanol composition suitable for use in ethanol-containing gasoline compositions from an ethanol composition comprising ethanol, water and acetic acid, wherein said process comprises contacting the ethanol composition with a desiccant bed comprising at least one porous inorganic oxide material at elevated temperature, wherein at least one of the porous inorganic oxide material(s) contains Brønsted acid sites and/or neutralised Brønsted acid sites.

The present invention also provides a process for reducing the butyric acid content of a butanol composition comprising at least one butanol, water and butyric acid, wherein said process comprises contacting the butanol composition with a desiccant bed comprising at least one porous inorganic oxide material at elevated temperature, wherein at least one of the porous inorganic oxide material(s) contains Brønsted acid sites and/or neutralised Brønsted acid sites.

The present invention also provides a process for the preparation of a fuel butanol composition suitable for use in butanol-containing gasoline compositions from a butanol composition comprising at least one butanol, water and butyric acid, wherein said process comprises contacting the butanol composition with a desiccant bed comprising at least one porous inorganic oxide material at elevated temperature, wherein at least one of the porous inorganic oxide material(s) contains Brønsted acid sites and/or neutralised Brønsted acid sites.

The present invention also provides a method of increasing the specific energy content of an alcohol composition comprising at least one alcohol having one to four carbon atoms, water and at least one carboxylic acid having from one to four carbon atoms, said method comprises contacting the alcohol composition with a desiccant bed comprising at least one porous inorganic oxide material at elevated temperature, wherein at least one of the porous inorganic oxide material(s) contains Brønsted acid sites and/or neutralised Brønsted acid sites.

The present invention also provides the use of a desiccant selected from molecular sieve 3A, molecular sieve 4A and mixtures thereof, for reducing the carboxylic acid content of an alcohol composition comprising an alcohol, water and a carboxylic acid in a process for drying said alcohol composition, wherein the process for drying said alcohol composition comprises contacting the alcohol composition, preferably in the vapour phase, at elevated temperature with a desiccant bed comprising a desiccant selected from molecular sieve 3A, molecular sieve 4A and mixtures thereof.

The present invention also provides the use of a desiccant selected from molecular sieve 3A, molecular sieve 4A and mixtures thereof, for reducing the acetic acid content of an ethanol composition comprising ethanol, water and acetic acid in a process for drying said ethanol composition, wherein the process for drying said ethanol composition comprises contacting the ethanol composition, preferably in the vapour phase, at elevated temperature with a desiccant bed comprising a desiccant selected from molecular sieve 3A, molecular sieve 4A and mixtures thereof.

The present invention also provides the use of a desiccant selected from molecular sieve 3A, molecular sieve 4A and mixtures thereof, for reducing the butyric acid content of a butanol composition comprising at least one butanol, water and butyric acid in a process for drying said butanol composition, wherein the process for drying said butanol composition comprises contacting the butanol composition, preferably in the vapour phase, at elevated temperature with a desiccant bed comprising a desiccant selected from molecular sieve 3A, molecular sieve 4A and mixtures thereof.

The alcohol composition to be treated in the process of the present invention comprises at least one alcohol having one to four carbon atoms, water and at least one carboxylic acid having from one to four carbon atoms. Preferably, the alcohol composition to be treated in the process of the present invention comprises at least one alcohol having two to four carbon atoms, water and at least one carboxylic acid having from two to four carbon atoms.

In one particular embodiment of the present invention, the alcohol composition to be treated comprises at least 90 wt % alcohol(s), preferably the alcohol composition comprises at least 93 wt % alcohol(s), more preferably the alcohol composition comprises at least 95 wt % alcohol(s).

In one particular embodiment of the present invention, the alcohol composition to be treated in the process of the present invention comprises ethanol, water and at least one carboxylic acid having from one to four carbon atoms.

In a specific embodiment wherein the alcohol composition to be treated in the process of the present invention comprises ethanol, the alcohol composition comprises a greater amount of ethanol (on a weight basis) than the total amount of other alcohols present in the alcohol composition. Therefore, in this embodiment, the alcohol composition to be treated in the process of the present invention is an ethanol composition comprising ethanol, water and at least one carboxylic acid having from one to four carbon atoms; optionally the ethanol composition may contain one or more other alcohols, in particular, selected from methanol, propanol(s) and butanol(s).

In the embodiment wherein the alcohol composition to be treated is an ethanol composition, said ethanol composition may also contain other alcohols, however, preferably at least 85 wt % of the alcohols present in the alcohol composition is ethanol, more preferably at least 90 wt % of the alcohols present in the alcohol composition is ethanol, even more preferably at least 95 wt % of the alcohols present in the alcohol composition is ethanol.

In one particular embodiment, the alcohol composition to be treated in the process of the present invention is an ethanol composition comprising ethanol, water and at least one carboxylic acid having from one to four carbon atoms, wherein said ethanol composition comprises at least 90 vol % ethanol, preferably at least 93 vol % ethanol, more preferably at least 95 vol % ethanol, such as 95.6 vol % ethanol, based on the total ethanol composition. In one specific embodiment of the present invention wherein the alcohol composition to be treated is an ethanol composition, said ethanol composition comprises an amount of water and an amount of the carboxylic acid which cannot be further reduced by distillation.

In another particular embodiment of the present invention, the alcohol composition to be treated in the process of the present invention comprises at least one butanol, water and at least one carboxylic acid having from one to four carbon atoms.

In a specific embodiment wherein the alcohol composition to be treated in the process of the present invention comprises at least one butanol, the alcohol composition comprises a greater amount of butanol(s) (on a weight basis) than the total amount of other alcohols present in the alcohol composition. Therefore, in this embodiment, the alcohol composition to be treated in the process of the present invention is a butanol composition comprising at least one butanol, water and at least one carboxylic acid having from one to four carbon atoms; optionally the butanol composition may contain one or more other alcohols.

In the embodiment wherein the alcohol composition to be treated is a butanol composition, said butanol composition may also contain other alcohols, however, preferably at least 85 wt % of the alcohols present in the butanol composition is butanol(s), more preferably at least 90 wt % of the alcohols present in the butanol composition is butanol(s), even more preferably at least 95 wt % of the alcohols present in the butanol composition is butanol(s).

In one particular embodiment, the alcohol composition to be treated in the process of the present invention is a butanol composition comprising water and at least one carboxylic acid having from one to four carbon atoms, wherein said butanol composition comprises at least 90 vol % butanol, preferably at least 93 vol % butanol, more preferably at least 95 vol % butanol, based on the total alcohol composition. In one specific embodiment of the present invention wherein the alcohol composition to be treated is a butanol composition, said butanol composition comprises an amount of water and an amount of the carboxylic acid which cannot be further reduced by distillation.

In one particular embodiment of the present invention, the alcohol composition to be treated comprises at most 1 wt % carboxylic acid(s), preferably at most 0.5 wt % carboxylic acid(s), and typically at most 0.25 wt % carboxylic acid(s); independently of the maximum stated amounts of carboxylic acid(s) in this embodiment, the alcohol composition to be treated comprises at least 25 ppm by weight carboxylic acid(s), preferably at least 50 ppm by weight carboxylic acid(s), more preferably at least 100 ppm by weight carboxylic acid(s), even more preferably at least 250 ppm by weight carboxylic acid(s), and typically at least 500 ppm by weight carboxylic acid(s).

In one particular embodiment of the present invention, the alcohol composition to be treated in the process of the present invention is an alcohol composition comprising at least one alcohol having one to four carbon atoms, water and acetic acid. In the embodiment wherein the alcohol composition to be treated comprises acetic acid, said alcohol composition may also contain other carboxylic acids.

In the embodiment wherein the alcohol composition to be treated in the process of the present invention comprises acetic acid, said alcohol composition may also contain other carboxylic acids, however, preferably at least 85 wt % of the carboxylic acids present in the alcohol composition is acetic acid, more preferably at least 90 wt % of the carboxylic acids present in the alcohol composition is acetic acid, even more preferably at least 95 wt % of the carboxylic acids present in the alcohol composition is acetic acid.

In one particular embodiment of the present invention, the alcohol composition to be treated in the process of the present invention is an ethanol composition comprising ethanol, water and acetic acid, said ethanol composition may also contain other alcohols and/or carboxylic acids. Preferred amounts of ethanol and acetic acid present in such an ethanol composition are the same as the preferred amounts independently stated in relation to ethanol compositions and compositions comprising acetic acid.

In another particular embodiment of the present invention, the alcohol composition to be treated in the process of the present invention is an alcohol composition comprising at least one alcohol having one to four carbon atoms, water and butyric acid. In the embodiment wherein the alcohol composition to be treated comprises butyric acid, said alcohol composition may also contain other carboxylic acids.

In the embodiment wherein the alcohol composition to be treated in the process of the present invention comprises butyric acid, said alcohol composition may also contain other carboxylic acids, however, preferably at least 85 wt % of the carboxylic acids present in the alcohol composition is butyric acid, more preferably at least 90 wt % of the carboxylic acids present in the alcohol composition is butyric acid, even more preferably at least 95 wt % of the carboxylic acids present in the alcohol composition is butyric acid.

In one particular embodiment of the present invention, the alcohol composition to be treated is a butanol composition comprising at least one butanol, water and butyric acid, said butanol composition may also contain other alcohols and/or carboxylic acids. Preferred amounts of butanol(s) and butyric acid present in such a butanol composition are the same as the preferred amounts independently stated in relation to butanol compositions and compositions comprising butyric acid.

In one particular embodiment of the present invention, the alcohol composition to be treated comprises at most 10 wt % water, preferably the alcohol composition comprises at most 7 wt % water, more preferably the alcohol composition comprises at most 5 wt % water; independently of the maximum stated amounts of water in this embodiment, the alcohol composition to be treated comprises at least 100 ppm by weight water, preferably at least 250 ppm by weight water, more preferably at least 500 ppm by weight water, and typically at least 1000 ppm by weight water.

In the process of the present invention, the alcohol composition to be treated is contacted with a desiccant bed comprising at least one porous inorganic oxide material at elevated temperature. At least one of the porous inorganic oxide material(s), preferably all of the porous inorganic oxide material(s), in the desiccant bed contains Brønsted acid sites and/or neutralised Brønsted acid sites.

In one particular embodiment of the present invention, the majority of the Brønsted acid sites in the porous inorganic oxide material(s) are neutralised Brønsted acid sites. In yet another particular embodiment of the present invention, essentially all of the Brønsted acid sites in the porous inorganic oxide material(s) are neutralised Brønsted acid sites. Neutralisation of Brønsted acid sites in porous inorganic materials is well known in the art and may be achieved through a variety of known techniques, such as ion exchange of the protons on the Brønsted acid sites with metal cations. Preferred metal cations that can be used as the counter ion on the neutralised Brønsted acid sites in the porous inorganic material(s) in the present invention are selected from the cations of the alkali metals; more preferably selected from the cations of lithium, sodium, potassium and mixtures thereof; even more preferably selected from the cations of sodium, potassium and mixtures thereof; most preferably selected from the cations of sodium and potassium.

The desiccant bed will typically be in the form of a bed of solid particulate material.

The desiccant bed may optionally comprise other materials in addition to the porous inorganic oxide material.

In one embodiment of the present invention, the desiccant bed is an admixture of a desiccant material and a porous inorganic oxide material containing Brønsted acid sites and/or neutralised Brønsted acid sites, wherein said porous inorganic oxide material containing Brønsted acid sites and/or neutralised Brønsted acid sites is different to the desiccant material. In this embodiment of the present invention, the desiccant material which is admixed with the porous inorganic oxide material may be any material which is useful as a desiccant in the drying of the alcohol composition to be treated in the present invention.

In another embodiment of the present invention, the desiccant bed consists of one or more porous inorganic oxide materials containing Brønsted acid sites and/or neutralised Brønsted acid sites, wherein one or more of said porous inorganic materials function as a desiccant when used in the alcohol composition to be treated in the present invention. By the term "function as a desiccant" it is meant that the porous inorganic oxide material(s) would absorb and/or adsorb water in the alcohol composition under process conditions.

In a preferred embodiment of the present invention, the porous inorganic oxide material is a porous inorganic oxide material comprising pores having a pore aperture of a size that would allow water to enter preferentially over the alcohols present in the alcohol composition; i.e. the pore aperture being of a size sufficiently large so as to allow water molecules to readily enter the pore, but sufficiently small so as to make it the pores less readily accessible to the alcohols present in the alcohol composition. The selection of the maximum pore size would be dependent upon the alcohols present in the alcohol composition.

In a more preferred embodiment of the present invention, the porous inorganic oxide material is a porous inorganic oxide material comprising pores having a pore aperture in the range of from 2.5 to 4.5 Å (0.25 to 0.45 nm).

In one particular embodiment, the porous inorganic oxide material at least one oxide of silicon, aluminum and mixtures thereof, preferably, the porous inorganic oxide material is an alumina-silicate; in a specific aspect of this embodiment, the porous inorganic oxide material comprises an alkali metal alumina-silicate, preferably the porous inorganic oxide material is an alkali metal alumina-silicate, more preferably selected from a potassium alumina-silicate, sodium alumina-silicate and mixtures thereof. In one particular embodiment of the present invention, the porous inorganic oxide material comprises at least one zeolite, more particularly, the porous inorganic oxide material comprises at least one material having a zeolite A framework.

In one particular embodiment of the present invention, the porous inorganic oxide material comprises a molecular sieve material, preferably selected from molecular sieve 3A, molecular sieve 4A and mixtures thereof.

Molecular sieve 3A (also referred to herein as 3A molecular sieve) is a molecular sieve having an effective pore opening of approximately 3A (0.3 nm) in diameter and is known in the art and are commercially available. Typically, molecular sieve 3A is a potassium form of the type "A" zeolite crystal structure, having a typical formula: $2/3K_2O.1/3Na_2O.Al_2O_3.2 SiO_2 \cdot 9/2 H_2O$ and a silica to alumina (SAR) ratio of approximately 2:1.

Molecular sieve 4A (also referred to herein as 4 Å molecular sieve) is a molecular sieve having an effective pore opening of approximately 4 Å (0.4 nm) in diameter and is known in the art and are commercially available. Typically, molecular sieve 4A is a sodium form of the type "A" zelite crystal structure, having a typical formula: $Na_2O.Al_2O_3.2SiO_2.9/2H_2O$ and a silica to alumina (SAR) ratio of approximately 2:1.

Both molecular sieve 3A and molecular sieve 4A are known to function as desiccants.

In one specific embodiment of the present invention, the porous inorganic oxide material comprises molecular sieve 3A; preferably, in this embodiment the porous inorganic oxide material is molecular sieve 3A.

In another specific embodiment of the present invention, the porous inorganic oxide material comprises molecular sieve 4A; preferably, in this embodiment the porous inorganic oxide material is molecular sieve 4A.

In one specific embodiment of the present invention, the desiccant bed consists of a porous inorganic oxide material selected from molecular sieve 3A, molecular sieve 4A and mixtures thereof.

The porous inorganic oxide material may comprise a binder material in addition to a porous inorganic oxide component. In the embodiments wherein the porous inorganic oxide material comprises a binder material, the binder material may be selected from any suitable binder material.

In the embodiments wherein the porous inorganic oxide material comprises a binder material, the binder material is preferably a refractory inorganic oxide such that the inorganic oxide is stable at high temperature, such as a temperature of at least 400° C., for example, a temperature in the range 400 to 550° C. In a preferred aspect of this embodiment of the present invention, the binder material is selected from at least one of the group of silicas, aluminas, silica-aluminas, titanias, magnesium silicates and magnesium aluminium silicates. Aluminas or silica-aluminas are particularly useful. Examples of suitable aluminas include boehmite type alumina and gamma alumina. Where a silica-alumina is used, its silica content is preferably in the range 5 to 40 wt %, suitably in the range 5 to 10 wt %. Preferably, the silica-alumina is amorphous.

In the embodiments wherein the porous inorganic oxide material comprises a binder material, the porosity of the binder material is preferably no greater than the porosity of the porous inorganic oxide component; in a particularly preferred aspect of the present invention, the binder material does not contain pores having a pore diameter greater than the pore diameter of the pores contained in the porous inorganic oxide component.

In the embodiments wherein the porous inorganic oxide material comprises a binder material, the amount of binder material present in the porous inorganic oxide material is preferably in the range of from 10 to 80 wt % and more preferably in the range of from 20 to 60 wt %.

In the embodiments wherein the porous inorganic oxide material comprises a binder material and a porous inorganic oxide component, the porous inorganic oxide component may be selected from inorganic oxide materials comprising pores having a pore aperture of a size that would allow water to enter preferentially over the alcohols present in the alcohol composition, as described above. Examples of suitable porous inorganic oxide components are porous inorganic oxide compounds having a pore aperture in the range of from 2.5 to 4.5 Å (0.25 to 0.45 nm); specific examples of suitable porous inorganic oxide components are molecular sieve materials, preferably selected from molecular sieve 3A, molecular sieve 4A and mixtures thereof.

In one specific embodiment wherein the porous inorganic oxide material comprises a binder material, the porous inorganic oxide component functions as a desiccant and the binder material comprises Brønsted acid sites and/or neutralised Brønsted acid sites. In such embodiments, the porous inorganic oxide component thereof will preferably also contain Brønsted acid sites and/or the neutralised Brønsted acid sites.

In another specific embodiment wherein the porous inorganic oxide material comprises a binder material, the porous inorganic oxide component comprises Brønsted acid sites and/or neutralised Brønsted acid sites and the binder material functions as a desiccant. In such embodiments, the porous inorganic oxide component thereof may also function as a desiccant and the binder material may also contain Brønsted acid sites and/or the neutralised Brønsted acid sites.

Whilst not wishing to be bound by theory, it is believed that the porous inorganic oxide material in the desiccant bed may adsorb some of the carboxylic acid and the Brønsted acid sites and/or the neutralised Brønsted acid sites of the material can act as a catalyst in the alcohol composition to esterify the carboxylic acid(s) with the alcohol(s) present in the alcohol composition. Additionally, the water that is formed during the esterification reaction would be adsorbed by the desiccant bed and, it is believed, will consequently disturb the chemical equilibrium of the esterification reaction in favour of the ester rather than the acid and alcohol.

Whilst not wishing to be bound by theory, it has been surprisingly observed that molecular sieves having pore apertures which would generally be considered too small for alcohols and/or carboxylic acids to enter exhibit the ability to reduce the amount of carboxylic acid present in the alcohol composition and form esters in the process of the present invention; for example molecular sieve 3A (having an approximate pore diameter of 3 Å) reducing the amount of acetic acid and producing ethyl acetate in ethanol compositions comprising ethanol, water and acetic acid, wherein the molecular diameters of both ethanol and ethanoic acid are generally believed to be greater the 3 Å.

Whilst the presence of acid(s) in alcohol compositions that are intended for use in or as fuels is either not desirable as they may be detrimental for the engine into which the fuel is introduced or the amount of acid(s) permissible in the fuel is restricted due to the specifications which must be met by the fuel, the presence of esters in alcohol compositions that are intended for use in or as fuels is more acceptable in the final fuel alcohol composition than acid(s), since such compounds are not considered as being as detrimental to engines as acids, and esters have a higher calorific value than the corresponding acids. Accordingly, it is desirable according to at least some embodiments of the present invention that the molecular sieve esterifies any acid(s) present, rather than simply adsorbs it/them, for example by converting acetic acid into ethyl acetate. In addition to providing the benefit of reducing carbon loss as described above, it is also believed, without wishing to be bound by theory, that esterifying carboxylic acid present in an alcohol feed (e.g. ethanol feed) also enables the resultant ester to return to the alcohol product (e.g. ethanol product) rather than remaining adsorbed to the desiccant bed (e.g. molecular sieve). Accordingly, there is less acid build-up on the desiccant bed which therefore prolongs the desiccant bed lifetime and hence reduces the requirement to regenerate the desiccant bed.

It is believed that the process of the present invention does not lead to the co-production of ethers (or would lead to only minimal co-production of ethers if any ethers are produced in the process of the present invention); this is advantageous in the treatment of alcohol compositions for use in gasoline as the lower boiling point of ethers relative to the boiling point of the corresponding alcohols and esters, may lead to a reduced maximum blending quantity of the alcohol composition in order to meet vapour pressure requirements for the gasoline composition.

Whilst not wishing to be bound by theory, it is believed that neutralised Brønsted acid sites may have less propensity to form ethers in the process of the present invention compared to protonated Brønsted acid sites. Thus, a further embodiment of the present invention provides the use of a desiccant bed comprising at least one porous inorganic oxide material, wherein at least one of the porous inorganic oxide material(s) contains Brønsted acid sites and essentially all of said Brønsted acid sites are neutralised Brønsted acid sites, preferably all of said Brønsted acid sites are neutralised Brønsted acid sites, for reducing the amount of ether(s) produced in a process for reducing the water and carboxylic acid content of an alcohol composition comprising at least one alcohol having one to four carbon atoms, water and at least one carboxylic acid having from one to four carbon atoms, wherein said process comprises contacting the alcohol composition with the desiccant bed at elevated temperature.

In the process of the present invention, the alcohol composition is brought in to contact with the desiccant bed at elevated temperature. In a preferred embodiment of the present invention, the alcohol composition is brought in to contact with the desiccant bed in the vapour phase at elevated temperature. By the term 'elevated temperature' it is meant a temperature which is greater than the ambient temperature.

Preferably, the temperature at which the alcohol composition is brought in to contact with the desiccant bed is a temperature of at least 70° C., more preferably at least 90° C., more preferably at least 110° C., even more preferably at least 120° C., and even more preferably at least 130° C., for example at least 140° C.

In specific embodiments of the present invention, the temperature at which the alcohol composition is brought in to contact with the desiccant bed is a temperature in a range defined by a combination of a lower temperature limit selected from 70° C., 90° C., 110° C., 120° C., 130° C., and 140° C., and an upper temperature limit selected from 250° C., 230° C., 220° C., 210° C., 200° C., and 190° C. (i.e. a temperature range selected from: 70° C. to 250° C.; 70° C. to 230° C.; 70° C. to 220° C.; 70° C. to 210° C.; 70° C. to 200° C.; 70° C. to 190° C.; 90° C. to 250° C.; 90° C. to 230° C.; 90° C. to 220° C.; 90° C. to 210° C.; 90° C. to 200° C.; 90° C. to 190° C.; 110° C. to 250° C.; 110° C. to 230° C.; 110° C. to 220° C.; 110° C. to 210° C.; 110° C. to 200° C.; 110° C. to 190° C.; 120° C. to 250° C.; 120° C. to 230° C.; 120° C. to 220° C.; 120° C. to 210° C.; 120° C. to 200° C.; 120° C. to 190° C.; 130° C. to 250° C.; 130° C. to 230° C.; 130° C. to 220° C.; 130° C. to 210° C.; 130° C. to 200° C.; 130° C. to 190° C.; 140° C. to 250° C.; 140° C. to 230° C.; 140° C. to 220° C.; 140° C. to 210° C.; 140° C. to 200° C.; and, 140° C. to 190° C.).

In the embodiments of the process of the present invention wherein the alcohol composition is brought into contact with the desiccant bed in the vapour phase, the process is preferably operated at a pressure such that the alcohol composition is in the vapour phase at the temperature at which it is contacted with the desiccant bed.

In the embodiments of the process of the present invention wherein the alcohol composition is brought in to contact with the desiccant bed in the vapour phase, the pressure at which the alcohol composition is brought in to contact with the desiccant bed in the vapour phase is a pressure of at least 0.15 MPa, more preferably at least 0.2 MPa, more preferably at least 0.3 MPa, even more preferably at least 0.4 MPa, and even more preferably at least 0.5 MPa.

In specific embodiments of the process of the present invention wherein the alcohol composition is brought in to contact with the desiccant bed in the vapour phase, the pressure at which the alcohol composition is brought in to contact with the desiccant bed in the vapour phase is a pressure in a range defined by a combination of a lower pressure limit selected from 0.15 MPa, 0.2 MPa, 0.3 MPa, 0.4 MPa, and 0.5 MPa, and an upper pressure limit selected from 5 MPa, 4 MPa, 3 MPa, 2 MPa and 1 MPa (i.e. a pressure range selected from: 0.15 MPa to 5 MPa; 0.15 MPa to 4 MPa; 0.15 MPa to 3 MPa; 0.15 MPa to 2 MPa; 0.15 MPa to 1 MPa; 0.2 MPa to 5 MPa; 0.2 MPa to 4 MPa; 0.2 MPa to 3 MPa; 0.2 MPa to 2 MPa; 0.2 MPa to 1 MPa; 0.3 MPa to 5 MPa; 0.3 MPa to 4 MPa; 0.3 MPa to 3 MPa; 0.3 MPa to 2 MPa; 0.3 MPa to 1 MPa; 0.4 MPa to 5 MPa; 0.4 MPa to 4 MPa; 0.4 MPa to 3 MPa; 0.4 MPa to 2 MPa; 0.4 MPa to 1 MPa; 0.5 MPa to 5 MPa; 0.5 MPa to 4 MPa; 0.5 MPa to 3 MPa; 0.5 MPa to 2 MPa; and, 0.5 MPa to 1 MPa).

Conveniently, the alcohol composition is brought in to contact with the porous inorganic oxide material by passing the alcohol composition through one or more desiccant beds comprising porous inorganic oxide material. Any configuration of system which brings a vapour or liquid phase composition in to contact with a bed of solid material may be employed.

In one particular embodiment of the process of the present invention, the process is performed in a system comprising a single desiccant bed, wherein the alcohol composition is brought in to contact with the desiccant bed by passing the alcohol composition through said single desiccant bed.

In another particular embodiment of the process of the present invention, the process is performed in a system comprising two or more sequential desiccant beds. In this embodiment, the alcohol composition is brought in to contact with the desiccant bed by passing the alcohol composition through two or more desiccant beds arranged sequentially, wherein the effluent from a first desiccant bed is passed through a second desiccant bed; optionally, the effluent from the second desiccant bed is passed through one or more subsequent desiccant beds.

The use of sequential beds would enable the use of different desiccant beds so that the adsorption of the water and the adsorption and/or esterification of the carboxylic acid(s) may be optimised.

In one particular embodiment of the process of the present invention, the process is performed in a system comprising two or more parallel desiccant beds. By the term "parallel beds" used herein, configurations comprising both traditional parallel beds as well as configurations comprising two or more beds which are not arranged in series and operate independently of each other, allowing the switching of the feed from one bed to the other (e.g. 'pressure swing' and 'temperature swing' systems), are encompassed by this term. In this embodiment, it is possible to contact the alcohol composition with the desiccant in at least one of the desiccant beds (the 'active bed(s)') whilst at least one of the other, parallel, desiccant beds is being regenerated (the 'regenerating bed(s)'). Operation of such systems would enable regeneration of the desiccant beds during operation of the process of the present invention through the use of systematic changing of the active and regenerating beds, such systematic changing of the active and regenerating beds may be automated or may be manually controlled, and the switching of the active and regenerating beds may be performed upon a predetermined schedule or may be performed through monitoring of the performance of the desiccant bed(s) through monitoring of the effluent stream from the active bed(s) and/or the regenerating bed(s).

In another embodiment of the process of the present invention, the process is performed in a system comprising two or more parallel desiccant beds and at least one desiccant bed which is sequentially arranged with one or more of the parallel beds.

The desiccant bed with which the alcohol composition is contacted will adsorb water, and possibly an amount of other oxygenate materials such as carboxylic acids, esters and alcohols, and, due to the increasing saturation of the desiccant bed, will reduce in efficiency as a desiccant over time. When sufficient reduction in efficiency as a desiccant occurs, the desiccant bed may either be replaced or regenerated; preferably, the desiccant bed is regenerated.

The determination of when to replace or regenerate the desiccant bed will depend on many factors, such as the maximum amount of water and/or acid acceptable in the effluent alcohol composition, which would vary depending upon the intended use of the alcohol composition.

The regeneration of the desiccant bed can be performed by any means known in the art for the regeneration of a desiccant material. Typically, the regeneration of the desiccant bed may be performed by contacting the desiccant bed with a carrier fluid containing essentially no water and either increasing the temperature of the desiccant to a temperature at which the water is desorbed from the desiccant bed into the carrier fluid or reducing the pressure to a pressure at which the water is desorbed from the desiccant bed into the carrier fluid; whilst the regeneration of the desiccant bed via means of increasing the temperature may be performed in both the liquid and the vapour phase, the regeneration of the desiccant bed via means of decreasing the pressure would be performed in the vapour phase only. A particularly convenient carrier fluid (either liquid phase or gas phase) which may be used for the regeneration of the desiccant bed is the dried alcohol which is effluent from the process of the present invention; alternative carrier fluids include other dry alcohols (either in the gas phase or liquid phase), dry alkanes (either in the gas phase or liquid phase), or gases which are inert in the desiccant bed, such as dry nitrogen and dry carbon dioxide.

In one embodiment of the present invention, the process is performed in a system comprising two or more parallel desiccant beds, wherein the alcohol composition is contacted with the desiccant bed in at least one of the desiccant beds (the 'active bed(s)') at the process temperature and pressure, whilst at least one of the other, parallel, desiccant beds is being regenerated (the 'regenerating bed(s)') by contacting a carrier fluid with the desiccant bed at an increased temperature relative to the active bed ("temperature swing adsorption"). In temperature swing adsorption systems operated in the gas phase, the pressure of both the active bed and the regenerating bed may be kept approximately constant. Advantageously, temperature swing adsorption systems may be operated entirely in the liquid phase. Operation of such systems would enable continuous regeneration of the desiccant beds through the use of systematic changing of the active and regenerating beds. Typical temperatures for regenerating the desiccant bed in temperature swing adsorption systems are temperatures having a minimum temperature of at least 180° C. and also being at least 10° C. greater than the process temperature; preferably, temperatures for regenerating the desiccant bed in temperature swing adsorption systems are temperatures having a minimum temperature of at least 200° C. and also being at least 15° C. greater than the process temperature; and, more preferably, temperatures for regenerating the desiccant bed in temperature swing adsorption systems are temperatures having a minimum temperature of at least at least 220° C. and also being at least 20° C. greater than the process temperature. By the term "process temperature", it is meant the temperature at which the alcohol composition is contacted with the desiccant bed in the process for reducing the amount of water and carboxylic acid of the alcohol composition (e.g. the temperature of the active bed). The heating of the desiccant bed in the regenerating bed may be achieved by preheating the carrier fluid prior to contacting it with the desiccant bed.

In one embodiment of the present invention, the process is performed in the vapour phase in a system comprising two or more parallel desiccant beds, wherein the alcohol composition is contacted with the desiccant bed in at least one of the desiccant beds (the 'active bed(s)') at the process temperature and pressure, whilst at least one of the other, parallel, desiccant beds is being regenerated (the 'regenerating bed(s)') by contacting a carrier gas with the desiccant bed at an decreased pressure relative to the active bed ("pressure swing adsorption"). In pressure swing adsorption systems, the temperature of both the active bed and the regenerating bed may be kept approximately constant. Operation of such systems would enable continuous regeneration of the desiccant beds through the use of systematic changing of the active and regenerating beds. Typical pressures for regenerating the desiccant bed in pressure swing adsorption systems are pressures having a maximum pressure of at most 0.2 MPa and also said pressure being at least 0.05 MPa lower than the process pressure; preferably, the pressures for regenerating the desiccant bed in pressure swing adsorption systems are pressures having a maximum pressure of at most 0.15 MPa and also said pressure being at least 0.075 MPa lower than the process pressure; and, more preferably, the pressures for regenerating the desiccant bed in pressure swing adsorption systems are pressures having a maximum pressure of at most 0.1 MPa and also said pressure being at least 0.1 MPa lower than the process pressure. By the term "process pressure", it is meant the pressure at which the alcohol composition is contacted with the desiccant bed in the process for reducing the amount of water and carboxylic acid of the alcohol composition (e.g. the pressure of the active bed).

Systems which employ a combination of temperature swing adsorption and pressure swing adsorption may also be used in the process of the present invention.

The time required for the regeneration of the porous inorganic oxide material will be dependent upon the various factors, such as the amount of water adsorbed, the exact desiccant bed used, the temperature and/or pressure used during the regeneration cycle, the carrier fluid used during the regeneration cycle as well as the flow rate of the carrier fluid during the regeneration cycle. The time required for the regeneration of the desiccant bed can be readily determined through means known in the art, for example, it may be determined by monitoring the water content in the effluent carrier fluid during a regeneration cycle or by monitoring the temperature of the porous inorganic oxide material during a regeneration cycle.

The effluent alcohol composition from the process of the present invention has a reduced content of water and carboxylic acid relative to the alcohol composition which is fed to the process of the present invention.

The effluent alcohol composition from the process of the present invention will typically have an increased content of esters relative to the alcohol composition which is fed to the process of the present invention, wherein said esters correspond to the esters formed through the reaction of the alcohol(s) and carboxylic acid(s) present in the alcohol composition which is fed to the process of the present invention.

As a result of the esterification process in combination with the removal of water, the specific energy content of the effluent alcohol composition will be increased relative to the specific energy content of the alcohol composition which is fed to the process of the present invention.

Therefore, the present invention further provides a method of increasing the specific energy content of an alcohol composition comprising at least one alcohol having one to four carbon atoms, water and at least one carboxylic acid having from one to four carbon atoms, said method comprises contacting the alcohol composition with a desiccant bed comprising at least one porous inorganic oxide material at elevated temperature, wherein at least one of the porous inorganic oxide material(s) contains Brønsted acid sites and/or neutralised Brønsted acid sites.

In one aspect of the present invention, the alcohol composition which results from the process of the present invention has a water content and the carboxylic acid content which meets required specifications for fuel alcohol compositions. Thus, in one particular aspect of the present invention, the process of the present invention provides a method for reducing the water and carboxylic acid content of an alcohol composition which contains a water and/or carboxylic acid content which is greater than is permissible in a fuel alcohol specification, such that the water and/or carboxylic acid content of the alcohol composition is equal to or lower than the maximum water and/or carboxylic acid content required by the fuel alcohol specification.

In another particular aspect of the present invention, the process of the present invention provides a method for reducing the acetic acid content of an ethanol composition comprising ethanol, water and acetic acid, wherein said process comprises contacting the ethanol composition with a desiccant bed comprising at least one porous inorganic oxide material at elevated temperature, wherein at least one of the porous inorganic oxide material(s) contains Brønsted acid sites and/or neutralised Brønsted acid sites.

In another particular aspect of the present invention, the process of the present invention provides a process for the preparation of a fuel ethanol composition suitable for use in ethanol-containing gasoline compositions from an ethanol composition comprising ethanol, water and acetic acid, wherein said process comprises contacting the ethanol composition with a desiccant bed comprising at least one porous inorganic oxide material at elevated temperature, wherein at least one of the porous inorganic oxide material(s) contains Brønsted acid sites and/or neutralised Brønsted acid sites.

In another particular aspect of the present invention, the process of the present invention provides a method for reducing the butyric acid content of a butanol composition comprising at least one butanol, water and butyric acid, wherein said process comprises contacting the butanol composition with a desiccant bed comprising at least one porous inorganic oxide material at elevated temperature, wherein at least one of the porous inorganic oxide material(s) contains Brønsted acid sites and/or neutralised Brønsted acid sites.

In another particular aspect of the present invention, the process of the present invention provides a process for the preparation of a fuel butanol composition suitable for use in butanol-containing gasoline compositions from a butanol composition comprising at least one butanol, water and butyric acid, wherein said process comprises contacting the butanol composition with a desiccant bed comprising at least one porous inorganic oxide material at elevated temperature, wherein at least one of the porous inorganic oxide material(s) contains Brønsted acid sites and/or neutralised Brønsted acid sites.

Without wishing to be bound by theory, it is believed that the desiccant bed may have a limited adsorbency capacity for esters that have been formed in the process of the present invention and/or the esters may pass through the desiccant bed at a slower rate than their corresponding alcohols. Thus, in an alternative embodiment of the invention, the process of the present invention is performed in a system comprising parallel desiccant beds, and the cycling between the desiccant bed being the active bed and the regenerating bed being performed on a sufficiently short time scale that the amount of esters present in the effluent alcohol composition is very low.

In one specific aspect of the present invention, the alcohol composition which results from the process of the present invention is an ethanol composition having a water content and the acetic acid content which meets required specifications for fuel ethanol compositions.

In one specific aspect of the present invention, the present invention provides the use of a desiccant selected from molecular sieve 3A, molecular sieve 4A and mixtures thereof, for reducing the carboxylic acid content of an alcohol composition comprising an alcohol, water and a carboxylic acid in a process for drying said alcohol composition, wherein the process for drying said alcohol composition comprises contacting the alcohol composition, preferably in the vapour phase, at elevated temperature with a desiccant bed comprising a desiccant selected from molecular sieve 3A, molecular sieve 4A and mixtures thereof.

In another specific aspect of the present invention, the present invention provides the use of a desiccant selected from molecular sieve 3A, molecular sieve 4A and mixtures thereof, for reducing the acetic acid content of an ethanol composition comprising ethanol, water and acetic acid in a process for drying said ethanol composition, wherein the process for drying said ethanol composition comprises contacting the ethanol composition, preferably in the vapour phase, at elevated temperature with a desiccant bed comprising a desiccant selected from molecular sieve 3A, molecular sieve 4A and mixtures thereof.

In another specific aspect of the present invention, the present invention provides the use of a desiccant selected from molecular sieve 3A, molecular sieve 4A and mixtures thereof, for reducing the butyric acid content of a butanol composition comprising at least one butanol, water and butyric acid in a process for drying said butanol composition, wherein the process for drying said butanol composition comprises contacting the butanol composition, preferably in the vapour phase, at elevated temperature with a desiccant bed comprising a desiccant selected from molecular sieve 3A, molecular sieve 4A and mixtures thereof.

The present invention will now be illustrated, without limiting the scope thereof, with reference to the following Examples and the accompanying Figures.

EXAMPLES

Equipment:
Pulsed Microreactor with Online GC-MS Analysis:
Agilent Technologies 7890A GC System+5975C inert XL MSD with Triple Axis detector. Column: Agilent 19091S-433:2127.54935 HP-5MS 5% Phenyl Methyl Silox 325° C.: 30 m×250 μm×0.25 μm.
Desiccants:
Merck Molecular Sieve 0.3 nm (3 Å), rods, ~1.6 mm (1/16"), 250 μm-500 μm sieved-fraction.
Sigma-Aldrich Molecular Sieves, 4 Å, beads, 8-12 mesh, 218 μm-500 μm sieved-fraction.
BDH AnalaR® Sodium Sulphate anhydrous granular, 218 μm-500 μm sieved-fraction
Ethanol: VWR AnalaR® NORMAPUR Ethanol Absolute
Water: Sigma-Aldrich ACS Water
Acetic Acid: ≥99.85% purity
Glass Wool: Supelco Analytical Pesticide Grade Glass Wool
Experimental The following examples were performed using a Pulsed Microreactor with online Gas Chromatography-Mass Spectrometry analysis. This equipment is similar to a conventional Gas Chromatography-Mass Spectrometer (GC-MS), except that the liner may be packed with solid material. Vaporised aliquots of a sample may be pulsed through the liner, with the effluent gas analysed by GC-MS. The parameters for the pulsed microreactor were as follows: Inlet: 17.588 psi, 100:1 split; Method: 40° C. oven for 6 minutes; Liner flow: 222.2 mL/min, GHSV 550533 hr$^{-1}$.

The glass liner of the Pulsed Microreactor was packed with 17 mg of the required desiccant, held in place by small glass wool bungs. For each experiment, 50 injections of a vaporised solution of 1020 ppmw acetic acid with 1.94 wt % water in ethanol was passed over the same sample, with the effluent stream analysed by GC-MS.

Comparative Example A

Control Experiment

To ensure that the process of vaporising an acetic acid/water/ethanol sample, passing it through glass wool in a glass liner, and then eluting on a GC-MS had little effect on the composition of the mixture (particularly did not result in significant loss of acetic acid, or esterification to ethyl acetate), a control experiment was performed. In the control experiment, the glass liner was packed with inert glass wool only (no molecular sieve), and a vaporised solution of 1020 ppmw acetic acid with 1.94 wt % water in ethanol pulsed through the liner.

Figure 1:
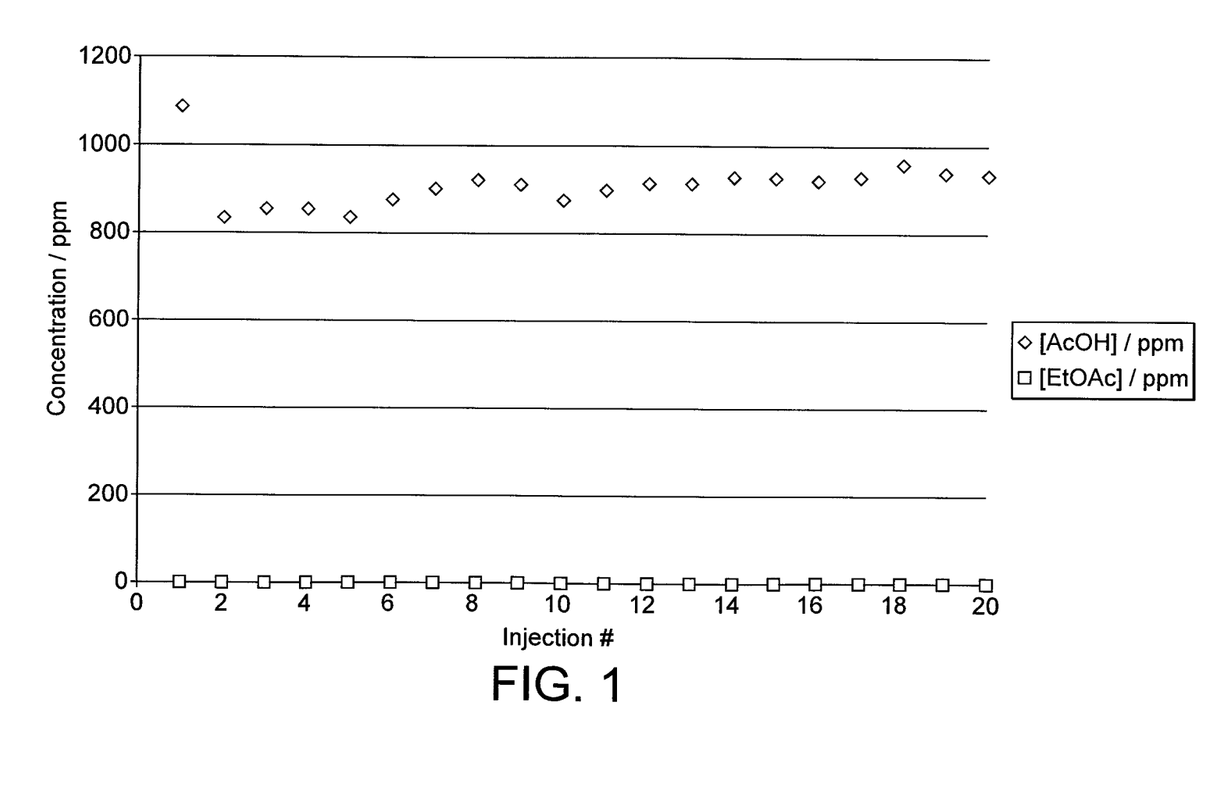
FIG. 1 provides a GC-MS (gas chromatography-mass spectrometry) plot for the control experiment wherein no desiccant was in the pulsed microreactor's glass liner through which the ethanol composition comprising water and acetic acid was passed.

The IGC-MS plot for the control experiment is provided in FIG. 1, which indicates that, within the uncertainty of the calibration, almost all of the initial 1020 ppmw of acetic acid is recovered from the process. In addition, no production of ethyl acetate has occurred. Thus, any changes seen in the experiments are as a direct result of the presence of the desiccant in the glass liner. The concentration of water in the effluent was too high for quantification on the MS-detector of the GC-MS.

Examples 1 and 2

Molecular Sieve Pore Size

For each of Examples 1 and 2, the inlet temperature of the Pulsed Microreactor was set to 120° C. In Example 1, 17 mg of the 3 Å molecular sieve desiccant was loaded in to the glass liner. In Example 2, 17 mg of the 4 Å molecular sieve desiccant was loaded in to the glass liner. The ethanol composition used in each of Examples 1 and 2 was a solution of 1020 ppmw acetic acid with 1.94 wt %.

For each of Examples 1 and 2, 50 injections of the ethanol composition were performed and the effluent from each injection was analysed by the online GC-MS. Between the injections, an inert carrier gas was passed through the liner and through the GCMS system. The effluent of the carrier gas injections was sufficiently dilute so as to not be not be quantifiable on the GC-MS.

Figure 2:
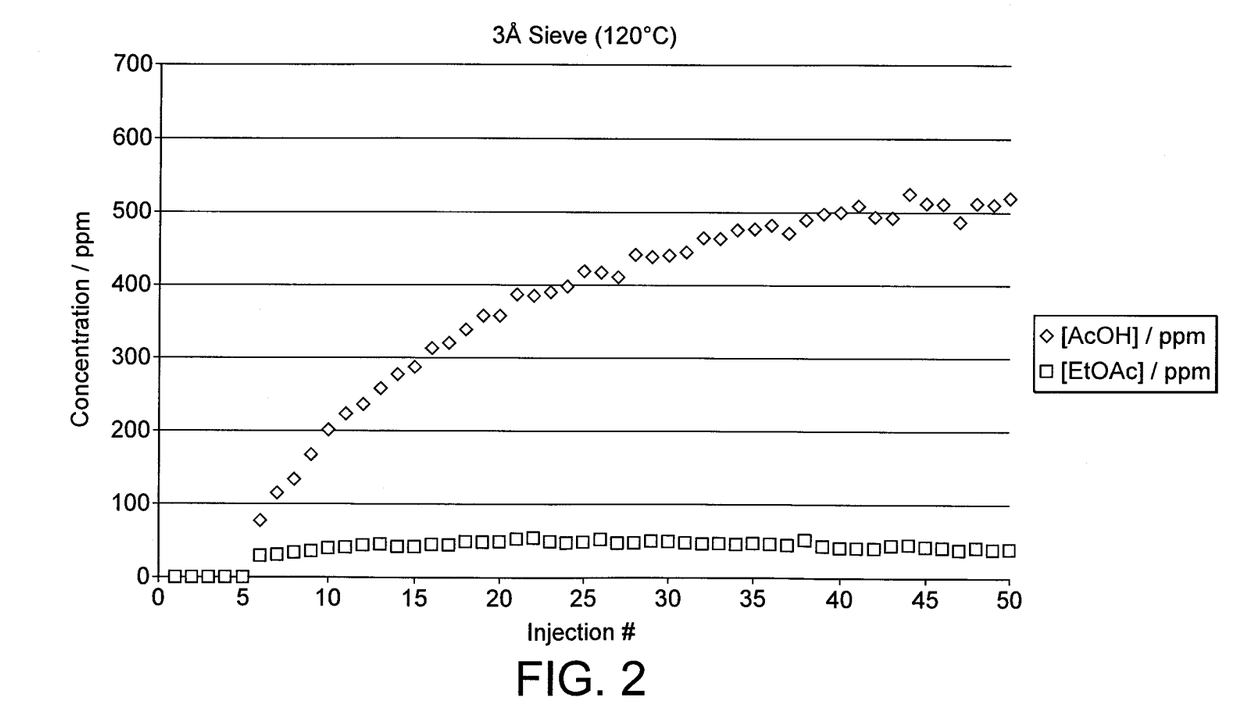
FIG. 2 provides a GC-MS plot wherein the desiccant in the pulsed microreactor's glass liner through which the ethanol composition comprising water and acetic acid was passed was a 3 Å molecular sieve.
Figure 3:
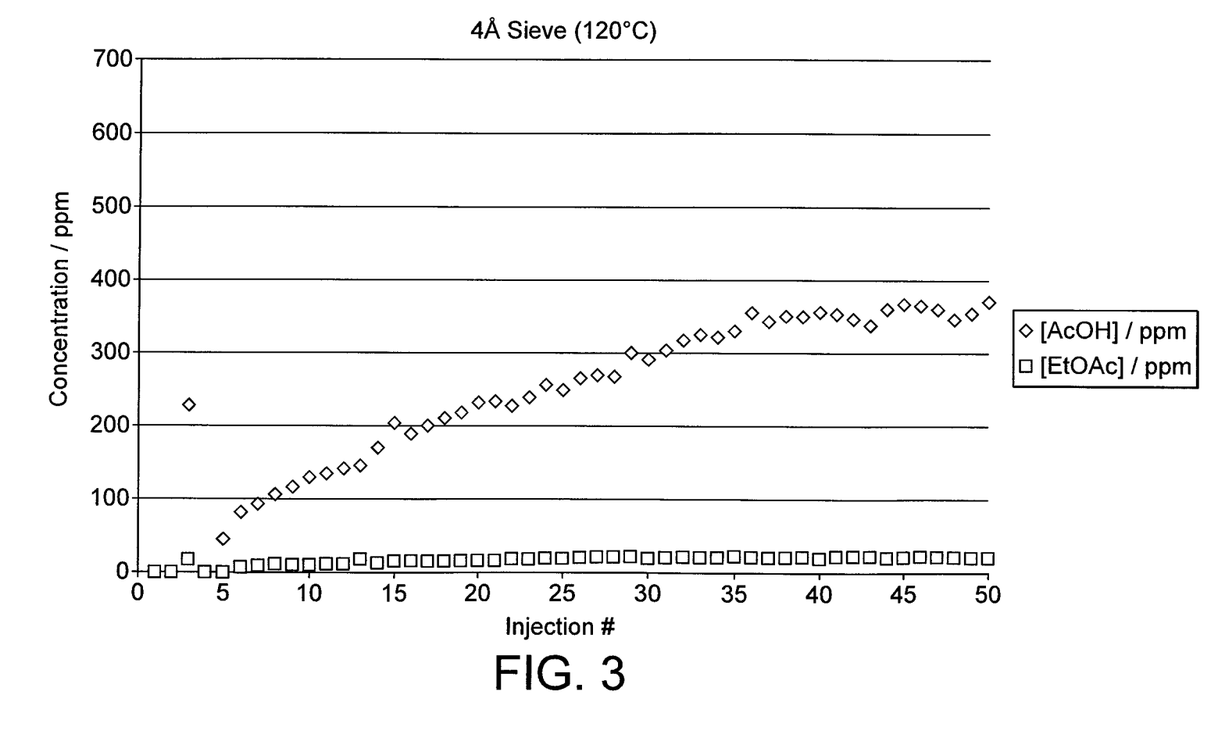
FIG. 3 provides a GC-MS plot wherein the desiccant in the pulsed microreactor's glass liner through which the ethanol composition comprising water and acetic acid was passed was a 4 Å molecular sieve.

The Pulsed Microreactor plots for Examples 1 and 2 (using the 3 Å and the 4 Å molecular sieves) are provided as FIGS. 2 and 3 respectively. Comparison of the results for the 3 Å and 4 Å molecular sieves at 120° C. indicates a broadly similar behaviour: gradual acid breakthrough to reach a steady-state value less than that injected, and esterification of part of the acetic acid to ethyl acetate. It can be seen that after 50 injections the 3 Å sieve approximately reaches a steady-state breakthrough of 500 ppmw acid, whereas the 4 Å sieve reaches only 400 ppmw.

Comparative Example B

Sodium Sulphate Desiccant

For Comparative Example B, the inlet temperature of the Pulsed Microreactor was set to 120° C. and 17 mg of the Sodium Sulphate desiccant was loaded in to the glass liner of the Pulsed Microreactor. The ethanol composition used in Comparative Example B was a solution of 1020 ppmw acetic acid with 1.94 wt % water in ethanol. In Comparative Example B, 40 injections of the ethanol composition were performed and the effluent from each injection was analysed. Between the injections, an inert carrier gas was passed through the liner and through the GCMS system. The effluent of the carrier gas injections was sufficiently dilute so as to not be not be quantifiable on the GC-MS.

Figure 4:
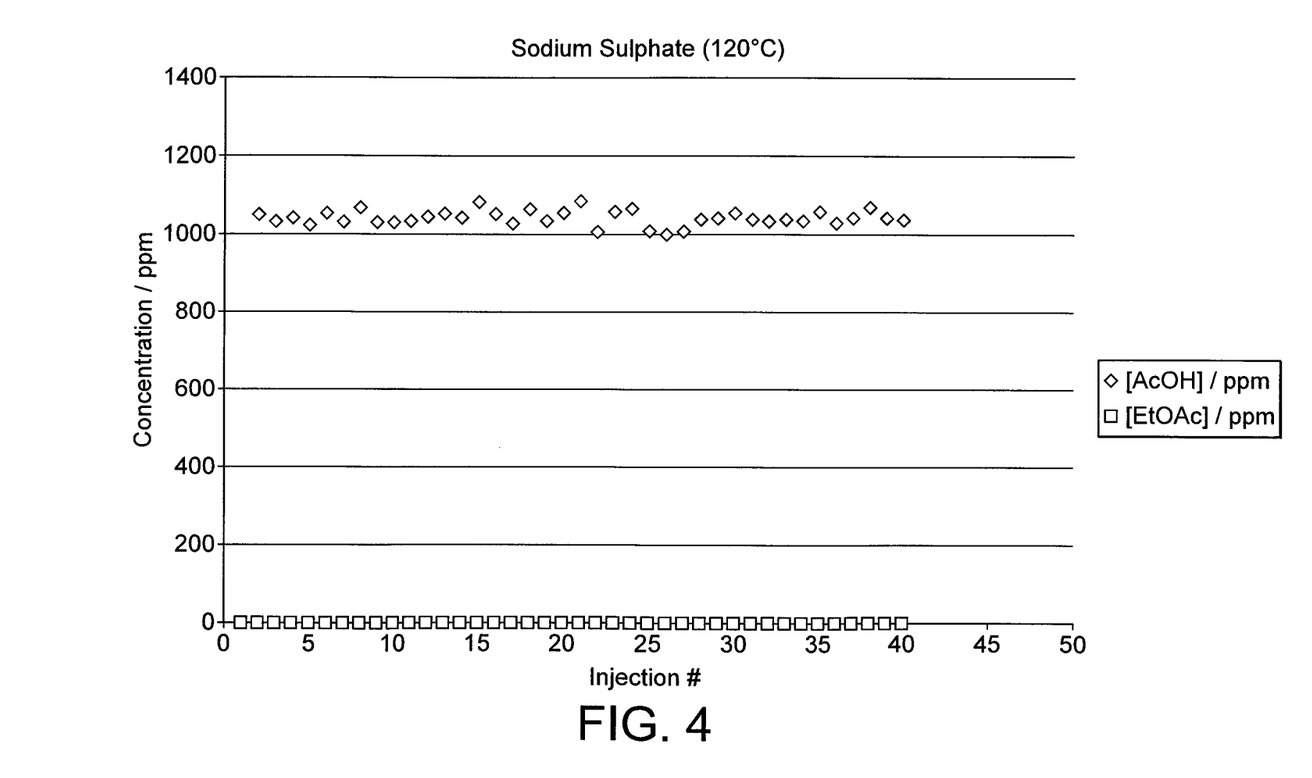
FIG. 4 provides a GC-MS plot wherein the desiccant in the pulsed microreactor's glass liner through which the ethanol composition comprising water and acetic acid was passed was sodium sulphate.

The GC-MS plot for Comparative Example B is provided as FIG. 4. The Pulsed Microreactor plot clearly demonstrates that over the course of 40 injections of acetic acid (1020 ppmw) and water (1.94 wt. %) in ethanol, the sodium sulphate neither perceptibly catalyses the esterification of acetic acid to ethyl acetate, nor adsorbs/absorbs the acetic acid with any great affinity. This is evidenced from the observation of, to within the uncertainty of the calibration, the full concentration of acetic acid passing into the GC-MS, and the lack of observed ethyl acetate.

Examples 3 to 7

Temperature Effects

For each of Examples 3 to 7, the effect of temperature on the concentration of acetic acid in the alcohol composition and the production of ethyl acetate was studied. In Example 3, 17 mg of the 3 Å molecular sieve desiccant was loaded in to the glass liner of the Pulsed Microreactor and the inlet temperature was set to 95° C.; in Example 4, 17 mg of the 3 Å molecular sieve desiccant was loaded in to the glass liner of the Pulsed Microreactor and the inlet temperature was set to 120° C.; in Example 5, 17 mg of the 3 Å molecular sieve desiccant was loaded in to the glass liner of the Pulsed Microreactor and the inlet temperature was set to 135° C.; in Example 6, 17 mg of the 3 Å molecular sieve desiccant was loaded in to the glass liner of the Pulsed Microreactor and the inlet temperature was set to 150° C.; and, in Example 7, 17 mg of the 3 Å molecular sieve desiccant was loaded in to the glass liner of the Pulsed Microreactor and the inlet temperature was set to 175° C. The ethanol composition used in each of Examples 3 to 7 was a solution of 1020 ppmw acetic acid with 1.94 wt % water in ethanol.

For each of Examples 3 to 7, 50 injections of the ethanol composition were performed and the effluent from each injection was analysed by GC-MS. Between the injections, an inert carrier gas was passed through the liner and through the GCMS system. The effluent of the carrier gas injections was sufficiently dilute so as to not be not be quantifiable on the GC-MS.

Figure 5:
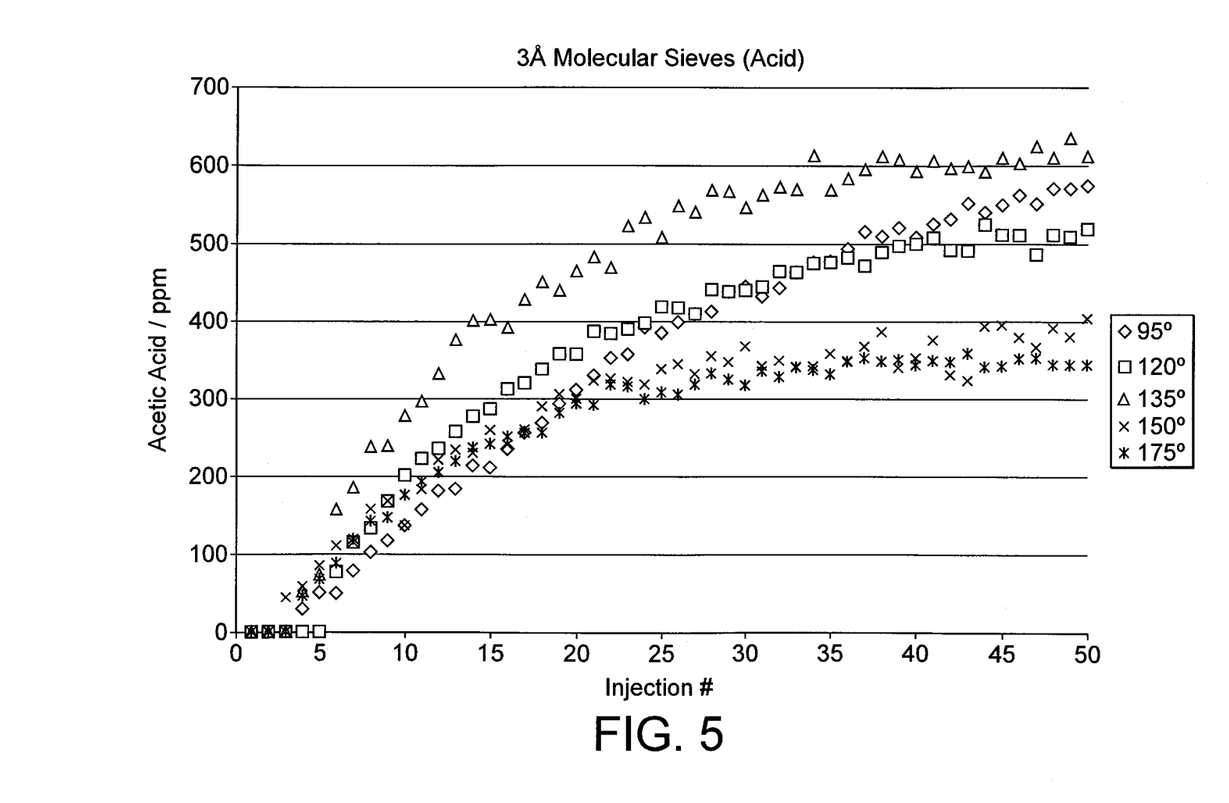
FIG. 5 provides GC-MS plots of acetic acid concentration in the effluent ethanol composition for five experiments, wherein in each experiment the pulsed microreactor was operated at a different inlet temperatures and wherein the desiccant in the IGC-MS glass liner through which the ethanol composition comprising water and acetic acid was passed in each experiment was a 3 Å molecular sieve.
Figure 6:
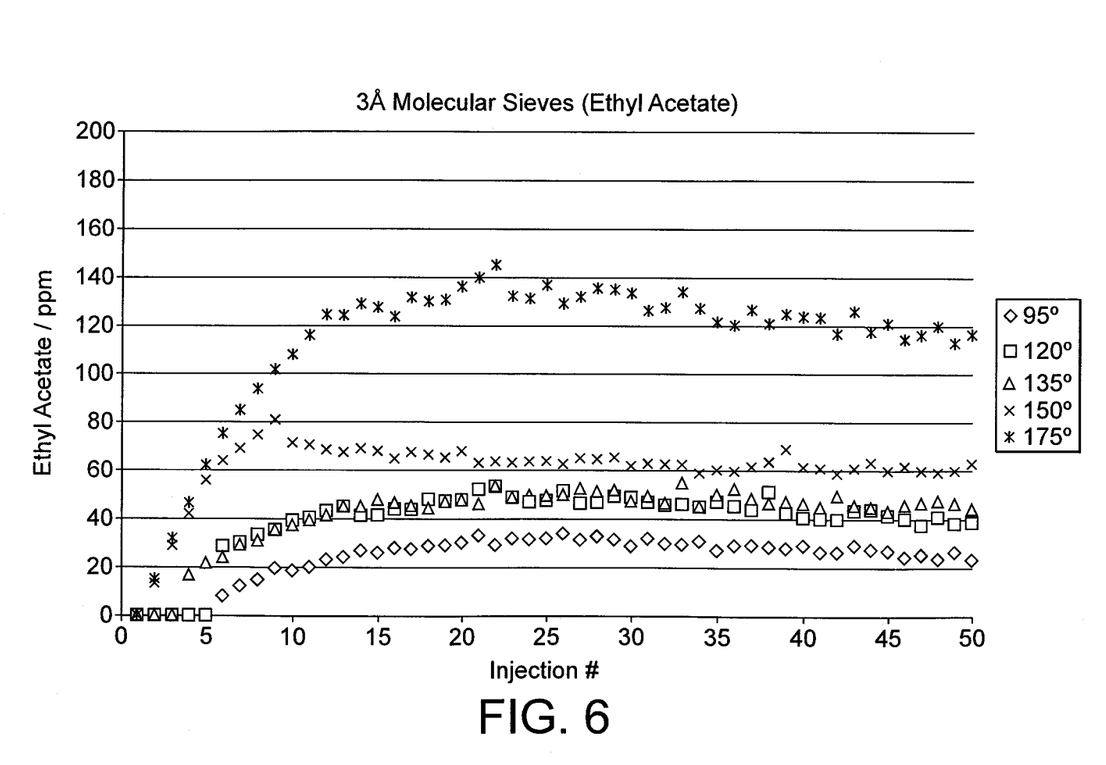
FIG. 6 provides GC-MS plots of acetic acid concentration in the effluent ethanol composition for five experiments, wherein in each experiment the pulsed microreactor was operated at a different inlet temperatures and wherein the desiccant in the IGC-MS glass liner through which the ethanol composition comprising water and acetic acid was passed in each experiment was a 3 Å molecular sieve.

For Examples 3 to 7, the GC-MS plots of the acetic acid concentration in the effluent and the ethyl acetate concentration in the effluent are provided as FIGS. 5 and 6 respectively. It can be seen from the results that a lower concentration of acid was observed in the effluent composition for the experiments performed at 150° C. and 170° C. and also the concentration of ethyl acetate observed in the effluent composition followed a general trend of increasing with increasing temperature.

Example 8

Ethanol Treatment

For Example 8, an ethanol feed was treated by passing over a molecular sieve: 3A Sigma Aldrich 208574 (beads, 4-8 mesh) having treated the sieve by washing with ethanol and drying at 200° C. for 12 hours. The ethanol feed was vapourised and passed over the molecular sieve at ~86° C. After passing over the molecular sieve, the pure ethanol product was condensed and collected. In total 9 Kg of the ethanol feed was processed. The initial molecular sieve was regenerated twice during the experiment by placing under slight nitrogen flow at a pressure of 20-30 mbara at a temperature of 100° C. for 2-3 hours.

Table 1 shows the ethanol, water, acetic acid and ethyl acetate composition of the ethanol feed, and the final ethanol product after passing over the molecular sieve. This indicates a drop in acetic acid and a rise in ethyl acetate.

TABLE 1

Analysis of the feed and product ethanols.

| Components | Ethanol Feed | Final Ethanol Product |
|---|---|---|
| Major Components (wt %) | | |
| Methanol | 0.16 | 0.14 |
| Ethanol | 96.53 | 99.4 |
| Water | 3.3 | 0.39 |
| Minor Components (ppm (wt)) | | |
| Ethyl Acetate | 4 | 40 |
| Acetic Acid | 33 | <5 |

A mass balance was performed on the acetic acid for this experiment, A total of 0.55 g of acetic acid was present in the ethanol feed. Of this 56 wt % was not vapourised and stayed in the feed reservoir and 0.17 wt % was recovered from the molecular sieve during regeneration. All of the remaining 3.99 mmol of acetic acid which passed over the molecular sieve was removed as there was no acetic acid detected in the ethanol product. This loss of 3.99 mmol correlates with the 3.91 mmol of ethyl acetate created as the ethanol passed over the molecular sieve and indicates that the majority of the acetic acid was being converted into ethyl acetate rather than being adsorbed by the molecular sieve.

The invention claimed is:

1. A process for reducing the water and carboxylic acid content of an alcohol composition comprising at least one alcohol having one to four carbon atoms, water and at least one carboxylic acid having from one to four carbon atoms, said process comprising contacting the alcohol composition with a desiccant bed comprising at least one porous inorganic oxide material at elevated temperature, wherein at least one of the porous inorganic oxide material(s) contains Brønsted acid sites and/or neutralised Brønsted acid sites.

2. A process according to claim 1, wherein the desiccant bed comprises an admixture of a desiccant material and a porous inorganic oxide material containing Brønsted acid sites and/or neutralised Brønsted acid sites, wherein said porous inorganic oxide material containing Brønsted acid sites and/or neutralised Brønsted acid sites is different to the desiccant material.

3. A process according to claim 1, wherein the desiccant bed consists of one or more porous inorganic oxide materials containing Brønsted acid sites and/or neutralised Brønsted acid sites and functions as a desiccant.

4. A process according to claim 1, wherein the desiccant bed comprises molecular sieve 3A, molecular sieve 4A and mixtures thereof.

5. A process according to claim 1, wherein the porous inorganic oxide material is at least partially in the form of the alkali metal salt.

6. A process according to claim 1, wherein the porous inorganic oxide material is at least partially in the protonated form.

7. A process according to claim 1, wherein the alcohol composition comprises ethanol.

8. A process according to claim 1, wherein the alcohol composition comprises acetic acid.

9. A process according to claim 7, wherein the alcohol composition comprises acetic acid.

10. A process according to claim 1, wherein the alcohol composition comprises at least one butanol.

11. A process according to claim 1, wherein the alcohol composition comprises butyric acid.

12. A process according to claim 1, wherein the alcohol composition is in the vapour phase when it is contacted with the desiccant bed.

13. A process according to claim 1, wherein the contacting of the alcohol composition with the desiccant bed is performed at a temperature in the range of from 70° C. to 250° C.

14. A process according to claim 13, wherein the contacting of the alcohol composition with the desiccant bed is performed at a temperature in the range of from 120 C to 210 C.

15. A process according to claim 14, wherein the contacting of the alcohol composition with the desiccant bed is performed at a temperature in the range of from 140 C to 190° C.

16. A process according to claim 1, wherein the contacting of the alcohol composition with the desiccant bed is performed at a pressure in the range of from 0.15 MPa to 5 MPa.

17. A process according to claim 1, wherein the concentration of water in the alcohol composition is in the range of from 1to 10 vol %.

18. A process according to claim 1, wherein the concentration of carboxylic acid in the alcohol composition is in the range of from 25 ppmw to 1 wt %.

19. A process for reducing the acetic acid content of an ethanol composition comprising ethanol, water and acetic acid, said process comprising contacting the ethanol composition with a desiccant bed comprising at least one porous inorganic oxide material at elevated temperature, wherein at least one of the porous inorganic oxide material(s) contains Brønsted acid sites and/or neutralised Brønsted acid sites.

20. A process according to claim 19, wherein the desiccant bed consists of a porous inorganic oxide material selected from molecular sieve 3A, molecular sieve 4A and mixtures thereof.

* * * * *